United States Patent
Sohn et al.

[19]

[11] Patent Number: 6,056,699
[45] Date of Patent: May 2, 2000

[54] APPARATUS FOR THE MEASUREMENT OF URETHRAL ANGLE CHANGE AND VESICAL PRESSURE

[75] Inventors: Ze'ev Sohn, D.N. Mod'in; Nahman Zimet, Tel Aviv, both of Israel

[73] Assignee: Influence Medical Technologies Limited, Israel

[21] Appl. No.: 08/850,164

[22] Filed: May 2, 1997

[30] Foreign Application Priority Data

May 5, 1996 [IL] Israel .......................................... 118154

[51] Int. Cl.⁷ ..................................................... A61B 5/00
[52] U.S. Cl. .............................. 600/561; 600/29; 128/885
[58] Field of Search .................................... 600/547, 561, 600/29–31, 38–40; 607/105

[56] References Cited

U.S. PATENT DOCUMENTS

| | | | |
|---|---|---|---|
| 3,496,942 | 2/1970 | Shipley | 607/105 |
| 5,012,822 | 5/1991 | Schwartz | 128/885 |
| 5,103,835 | 4/1992 | Yamada et al. | 600/547 |
| 5,423,329 | 6/1995 | Ergas | 600/546 |

*Primary Examiner*—Cary O'Connor
*Assistant Examiner*—Ryan Carter
*Attorney, Agent, or Firm*—Oppenheimer Wolff & Donnelly, LLP

[57] ABSTRACT

Apparatus for diagnosing urinary stress incontinence of a subject, including a substantially rigid, disposable probe insertable into the urethra of the subject, generally along a longitudinal axis of the urethra. A reusable sensor unit, is removably coupled to the probe, for sensing physiological parameters of the subject. The apparatus preferably includes a fluid pressure sensor, contained in the sensor unit, in pressure communication with a distal end of the probe. The probe includes a flexible diaphragm in fluid communication with the distal end. The diaphragm provides the pressure communication between the pressure sensor and the distal end while substantially preventing fluid communication between the distal end and the pressure sensor.

26 Claims, 5 Drawing Sheets

FIG. 2A
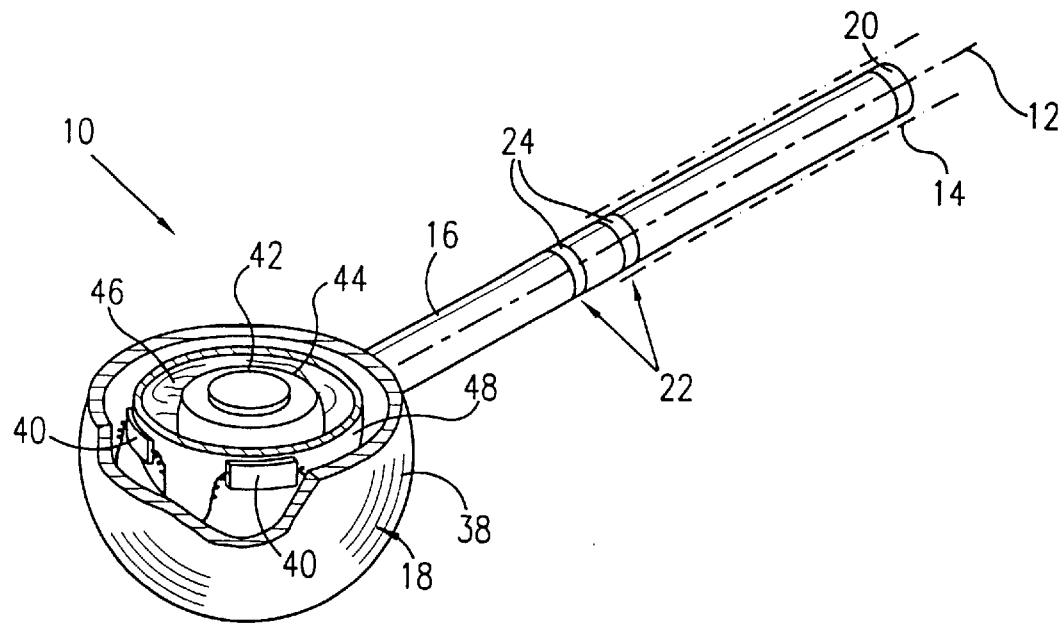
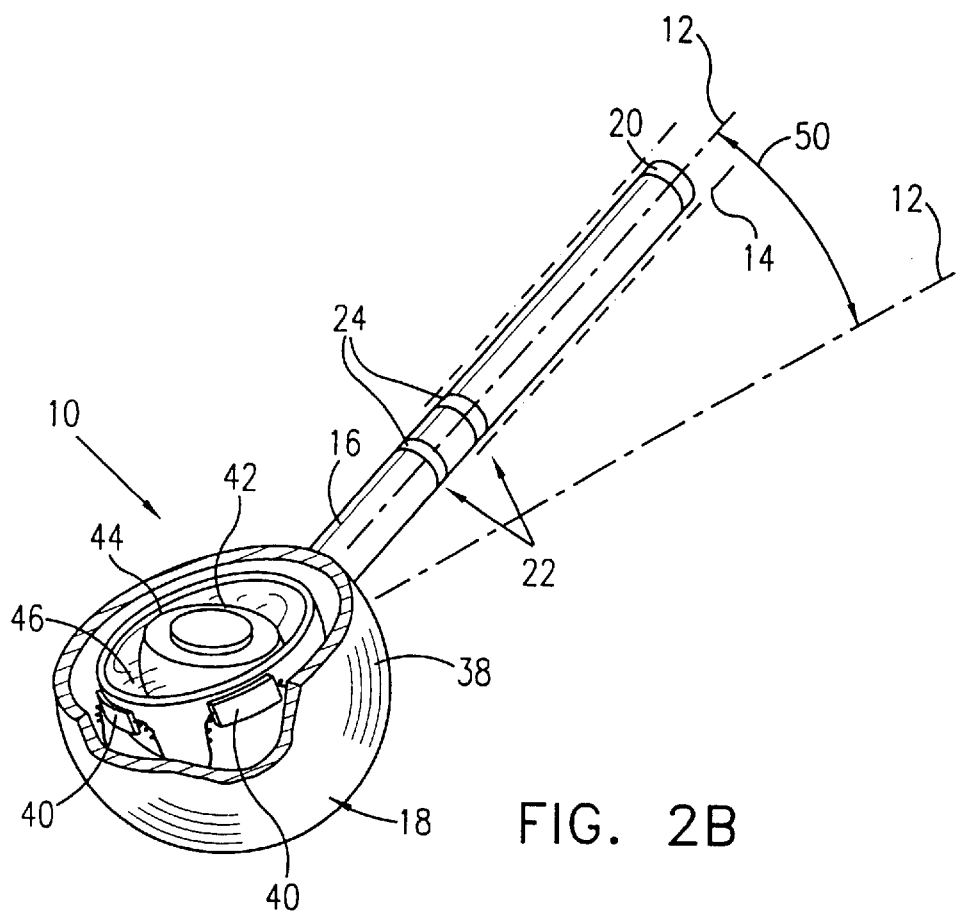
FIG. 2B

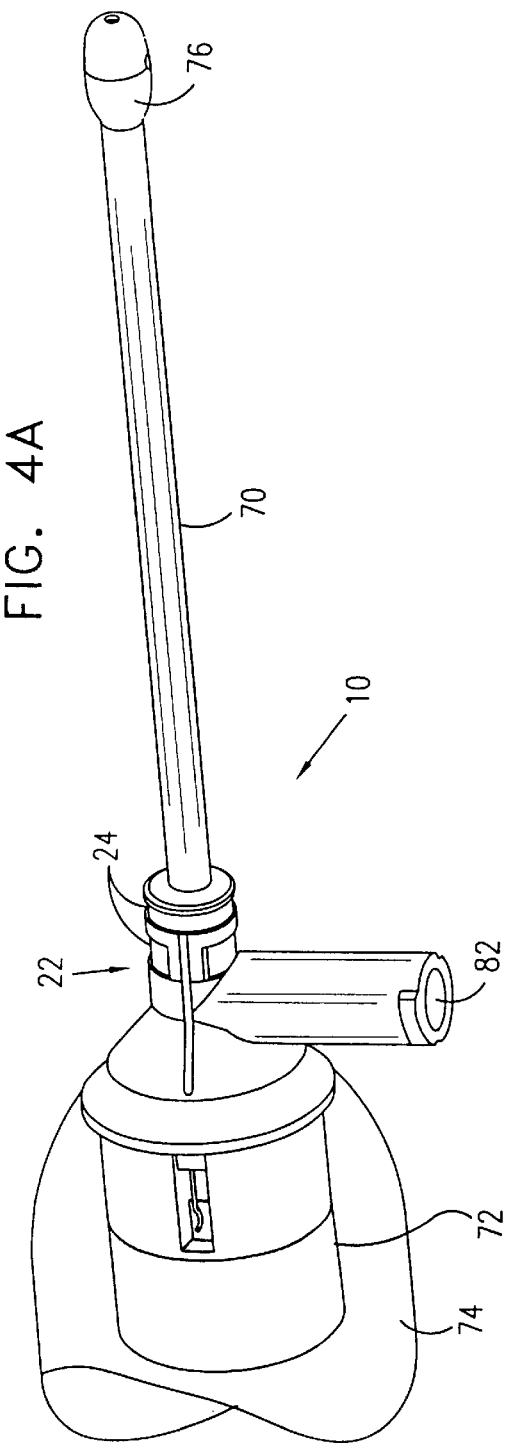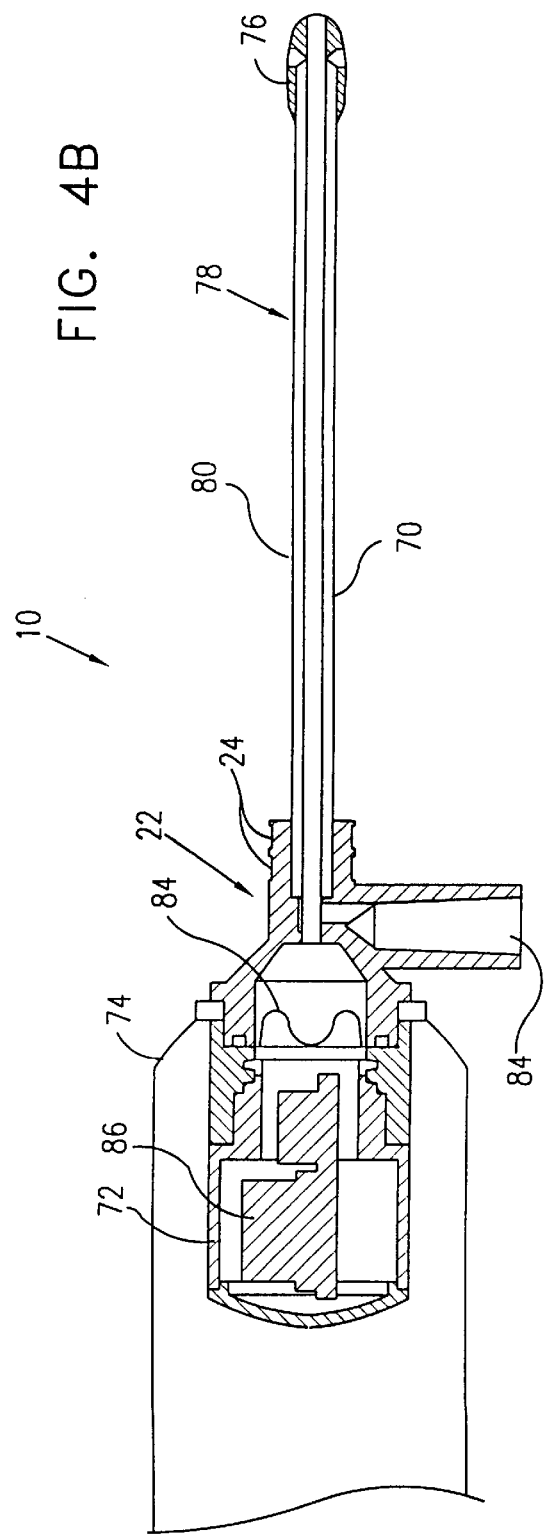

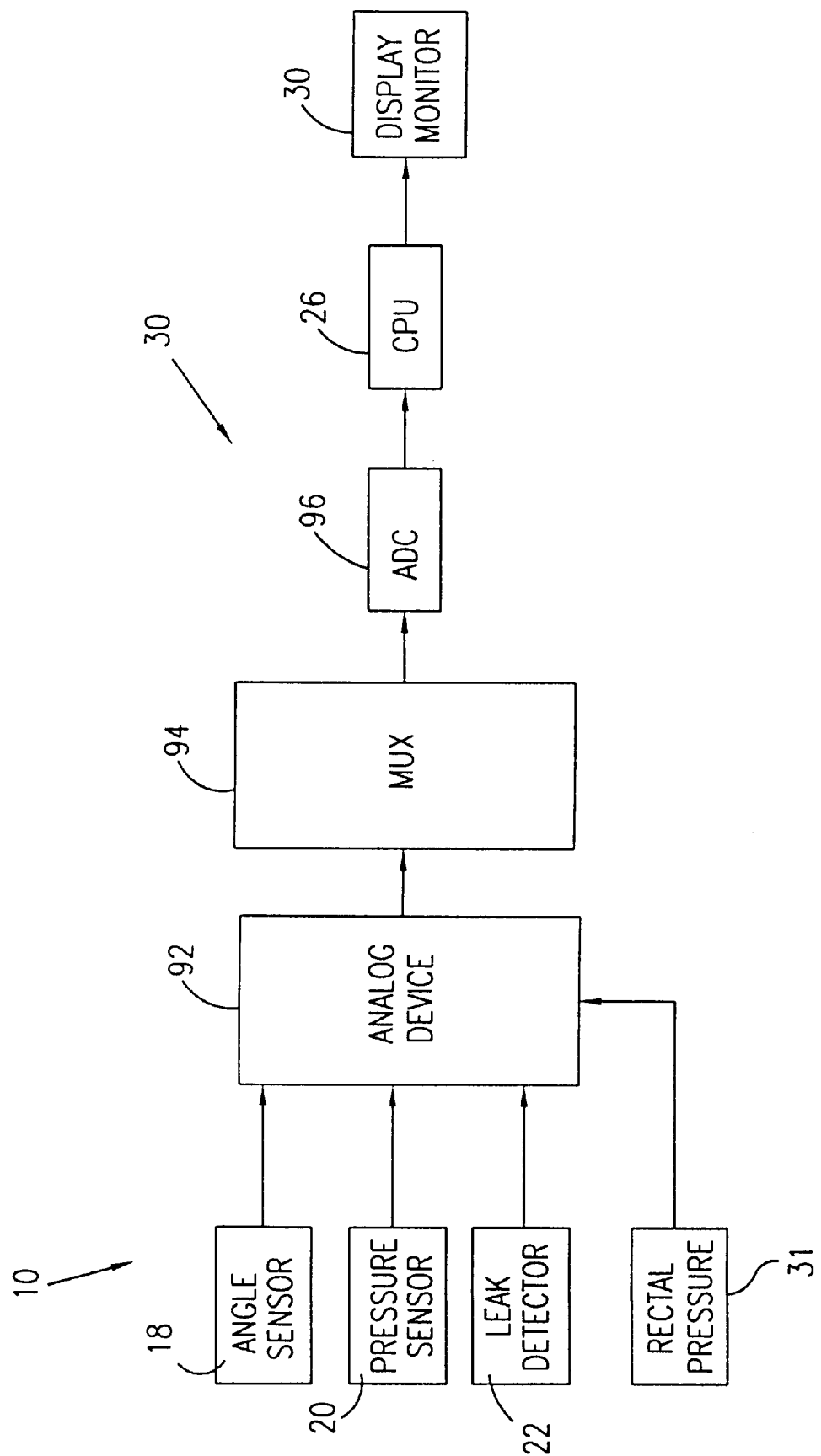

APPARATUS FOR THE MEASUREMENT OF URETHRAL ANGLE CHANGE AND VESICAL PRESSURE

FIELD OF THE INVENTION

The present invention relates to urinary apparatus generally and particularly to apparatus for the measurement of urethral angle change and vesical pressure.

BACKGROUND OF THE INVENTION

Female urinary stress incontinence is a pathology affecting more than ten percent of the female population over age 60. The pathology results from either one or both of the following anatomical conditions: 1) abdominal straining causing urethral hypermobility; 2) urethral intrinsic sphincter deficiency (ISD), which is the inability of urethral musculature to completely close the urethra or keep it closed during stress. The surgical procedures to correct these pathologies are dependent on whether urethral hypermobility or ISD is the predominant pathology. In the case of urethral hypermobility, incontinence is corrected by prevention of urethral descent during stress and/or abdominal straining. In the case of ISD, correction is accomplished by increasing the passive pressure applied on the urethra so as to increase its passive resistance to urine passage. Failure to determine the correct type of incontinence results in the performance of an inappropriate surgical procedure with subsequent unsatisfactory surgical success and subsequent complications.

To properly establish the type of urinary incontinence, two factors must be determined: 1) urethral descent during straining, which may be determined by measurement of the spatial angular change of the urethral axis (herein called the urethral angle change) during straining and 2) leak point pressure, the minimal vesical pressure at which urine leaks through the urethra. Low leak point pressure characterizes ISD. A common method in the art to evaluate urethral angle change is by installing a "rod" into the urethra with the physician estimating the rod axis angle change by visual examination. Leak point pressure is generally established during urodynamic evaluation by the placement of a pressure measuring catheter in the bladder with the physician recording the pressure at which urine leakage through the meatus is visually detected. Both these testing methods lack objectivity and accuracy in obtaining results. There is therefore a need for an invention which provides a more objective and accurate measurement of urethral angle change and leak point pressure concomitantly.

SUMMARY OF THE INVENTION

It is an object of the present invention to provide a probe and sensors for the measurement of urethral angle change and/or vesical pressure during abdominal straining.

In preferred embodiments of the present invention, a probe for insertion into the urethra of a subject, for use in diagnosis of urinary stress incontinence, comprises one or more angle sensors, a pressure sensor and a leakage detector.

In one embodiment of the invention, the angle sensor comprises a magnet which floats on the surface of liquid inside a ball-shaped cartridge to which sensors for measuring magnetic fields, or Hall effect devices, are attached. Each Hall effect device outputs a value related to its orientation with the magnet. These values are preferably transmitted by the Hall effect device to a CPU which calculates the angle changes of the probe from a predetermined reference. The CPU may then display the angle changes and any other pertinent information on a display screen of a monitor.

In another embodiment, the angle sensor comprises a conductive fluid, such as liquid mercury, in a chamber with a resistive element. The portion of the resistive element which is covered by fluid varies with the angle of the probe. The electrical resistance of the resistive element varies with the amount of the portion submerged in fluid. The measured resistance is transmitted to the CPU which converts the resistance into an angular value. The CPU processes different resistive values to determine the change in urethral angle.

In still other embodiments of the present invention, the angle sensor comprises a chip accelerometer, for example, Single Chip Accelerometer model ADXL05, produced by Analog Devices Inc. of Norwood, Mass. The use of such accelerometers in measuring tilt angle is known in the art. The pressure sensor is preferably located at the proximal end of the probe, but it may alternatively be located at or adjacent to the distal end.

The leakage detector is preferably a type of electrical conductivity sensor, which senses the presence of a leak of urine when the urine creates electrical contact between two conductive strips or rings on an outer surface of the probe.

In some preferred embodiments of the present invention, signals from the angle sensor, pressure sensor and leak detector are processed by an analog device and transmitted to a multiplexer. A central processing unit (CPU) samples data from the multiplexer preferably via an analog-to-digital converter. The CPU may alternatively sample data received from the sensors and leakage detector, process the data and display pertinent information on a monitor.

In one of these preferred embodiments, an additional pressure sensor is inserted into the subject's rectum. The rectal pressure sensor is processed, multiplexed and sampled by the CPU, as described above, which then displays rectal pressure data along with data from the other sensors.

There is therefore provided, in accordance with a preferred embodiment of the present invention, apparatus for diagnosing urinary stress incontinence of a subject, including:

a substantially rigid, disposable probe insertable into the urethra of the subject, generally along a longitudinal axis of the urethra; and a reusable sensor unit, removably coupled to the probe, for sensing physiological parameters of the subject.

Preferably, the apparatus includes a fluid pressure sensor in pressure communication with a distal end of the probe. Preferably, the pressure sensor is contained in the sensor unit, and the probe includes a flexible diaphragm in fluid communication with the distal end, which diaphragm provides the pressure communication between the pressure sensor and the distal end while substantially preventing fluid communication between the distal end and the pressure sensor.

Preferably, the probe contains first and second lumens communicating with the distal end thereof, the first lumen communicating at its proximal end with the diaphragm, and the second lumen communicating at its proximal end with a fluid port.

The apparatus preferably includes at least one spatial angle sensor coupled to the probe, so as to sense a change in an angular orientation thereof.

In a preferred embodiment of the present invention, the at least one angle sensor includes a magnet which floats on a liquid, and at least one Hall effect device located in propinquity with the magnet, wherein the change in angular orientation causes a corresponding movement of the magnet, which movement is detected by the at least one Hall effect device, thereby to sense the change.

In another preferred embodiment, the at least one angle sensor includes a resistive element partially immersed in a conductive fluid, wherein an amount of the element that is immersed changes in relation to the change in angular orientation, causing a resistive change responsive to the change in angular orientation.

Alternatively, the at least one angle sensor includes a chip accelerometer.

Preferably, a leakage detector is attached to the probe and detects the flow of a fluid along the probe. Preferably, the leakage detector includes an electrical conductivity sensor, most preferably including at least two conductive contacts on an outer surface of the probe, which detects presence of urine by sensing a change in conductivity due to urine contacting the sensor.

Preferably, the apparatus includes a flexible sleeve, fixed to the probe, which sleeve is extended over the sensor unit to prevent transfer of contaminants between the probe and the sensor unit.

In a preferred embodiment of the present invention, the apparatus includes a central processing unit (CPU) in communication with the sensor unit, for processing data received therefrom. Preferably, the CPU is in wired communication with the sensor unit. Alternatively, the apparatus includes a wireless transmitter, for transmitting data from the sensor unit to the CPU.

Preferably, a monitor in electrical communication with the CPU displays information provided by the CPU.

In a preferred embodiment of the present invention, the apparatus includes a rectal pressure sensor in communication with the CPU, which receives and processes data therefrom.

There is further provided, in accordance with a preferred embodiment of the present invention, a method for diagnosing urinary stress incontinence of a subject, the method including:
 coupling a sensor unit to a probe;
 inserting the probe into the urethra of the subject, generally along a longitudinal axis thereof;
 receiving signals from the sensor unit responsive to a change in pressure within the subject's bladder.

Preferably, coupling the sensor unit to the probe includes bringing a flexible diaphragm, in fluid communication with a distal end of the probe, into pressure communication with the sensor unit.

In a preferred embodiment of the present invention, the bladder is filled with fluid through a lumen in the probe, such that the fluid exerts a pressure on the diaphragm, and the pressure exerted on the diaphragm is measured.

Preferably, receiving signals from the sensor unit includes receiving signals responsive to an angular orientation of the probe, and the method includes measuring a change in the angular orientation responsive to the change in pressure. Preferably, an abdominal pressure of the subject is increased, thereby causing the angular orientation to change.

Further preferably, receiving signals from the sensor unit includes receiving signals responsive to leakage of urine from the bladder of the subject through the urethra.

Preferably, the data are analyzed to determine whether the urinary stress incontinence is related to urethral hypermobility or to ISD.

In a preferred embodiment of the present invention, the method also includes inserting a probe into the subject's rectum and receiving signals therefrom responsive to a rectal pressure.

BRIEF DESCRIPTION OF THE DRAWINGS

The present invention will be understood and appreciated more fully from the following detailed description, taken in conjunction with the drawings in which:

FIGS. 2A and 2B are simplified pictorial, partially cutaway illustrations of the apparatus of FIG. 1 with an angle sensor which comprises a Hall effect sensor, respectively before and after a spatial angle change in the urethral angle;

FIG. 4A is a simplified pictorial illustration of apparatus for intraurethral measurement, in accordance with another preferred embodiment of the present invention;

FIG. 4B is a schematic, sectional illustration of the probe of FIG. 4A; and

FIG. 5 is a simplified electronic block diagram of a CPU and monitor useful in the apparatus of FIG. 1.

DETAILED DESCRIPTION OF THE PREFERRED EMBODIMENTS

Figure 1:
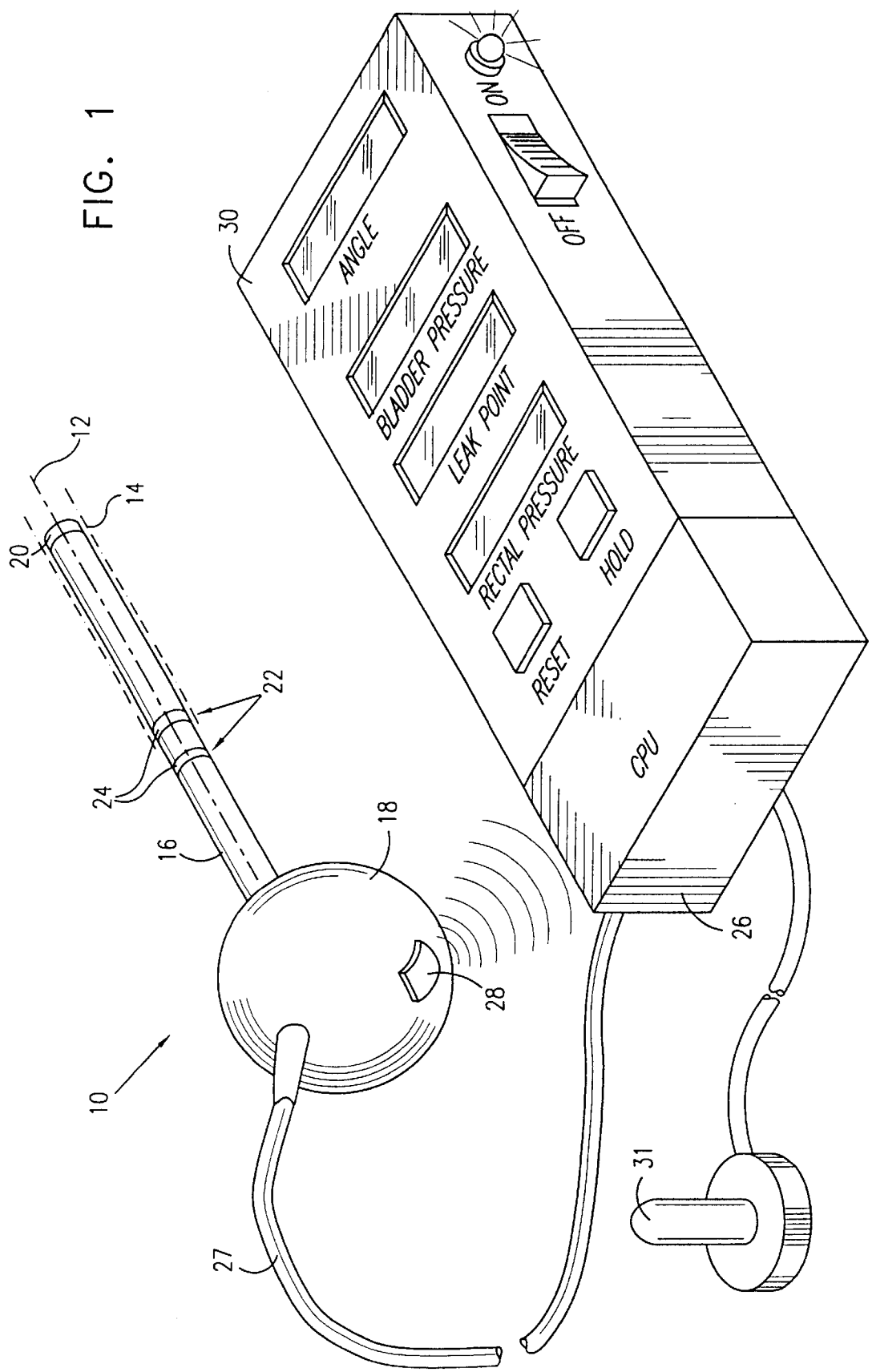
FIG. 1 is a simplified illustration of apparatus for intraurethral measurement, constructed and operative in accordance with a preferred embodiment of the present invention, for measurement of a change in the orientation axis of a urethra and diagnosis of urinary stress incontinence.

Reference is now made to FIG. 1 which illustrates apparatus 10, constructed and operative in accordance with a preferred embodiment of the present invention, for measurement of a spatial angle change of an orientation axis 12 of urethra 14 of a subject and diagnosis of urinary stress incontinence.

Apparatus 10 preferably includes a probe 16 which is suitably sized and shaped to be inserted into urethra 14. Probe 16 is preferably substantially rigid and constructed of a medically safe plastic or metal, such as polycarbonate or an austenitic stainless steel.

At least one spatial angle sensor 18 is preferably attached to probe 16, either at a proximal end of probe 16 as shown in FIG. 1, or alternatively at any other position along probe 16. Angle sensor 18, preferred embodiments of which will be described in greater detail hereinbelow, preferably senses changes in the angle of axis 12 relative to a reference, such as the gravitational vector or a horizontal plane.

A fluid pressure sensor 20 is preferably attached to a distal end of probe 16 for sensing fluid pressure of a bladder (not shown). Alternatively, pressure sensor 20 may be attached to the proximal end of probe 16 or to any other convenient location along the length of the probe, in which case sensor 20 is configured to measure the pressure at the distal end of probe 16, for example, by providing a lumen in the probe between sensor 20 and the distal end of the probe. Pressure sensor 20 may be any conventional type of miniature pressure sensor, such as a diaphragm or piezoelectric type of sensor, for example.

A leakage detector 22 is preferably attached to probe 16, most preferably on an outer surface of the probe adjacent angle sensor 18. Leakage detector 22 may be an electrical conductivity sensor which comprises two metallic rings 24. If urine leaks from the bladder, a stream of urine flows over rings 24 and reduces the electrical resistance between them. The urine leak can be detected by detecting the change in resistance.

Angle sensor 18, pressure sensor 20 and leakage detector 22 may be any sensor known in the art for sensing or measuring angles, pressures and leakage. In a preferred embodiment of the present invention, the angle sensor comprises one or more chip accelerometers, as are known in the art.

Angle sensor 18, pressure sensor 20 and leakage detector 22 are preferably in wired communication with a central processing unit (CPU) 26, such as by means of a cable 27. Alternatively, a transmitter 28 may be provided for wireless communication of the sensors 18 and 20 and detector 22 with CPU 26. Transmitter 28 may be mounted on the outside of angle sensor 18 or at the proximal end of probe 16, for example. Preferably a monitor 30 is electrically connected to CPU 26 for displaying information provided by CPU 26, such as urethral angle, bladder pressure, or leak point pressure, for example. CPU 26 and monitor 30 may be powered either by a battery or external power source (both not shown).

It will be appreciated that CPU 26 and monitor 30 may include other wired and/or wireless connections for receiving sensor inputs, as well as other function keys and display windows for processing and displaying information. In a preferred embodiment of the present invention, shown in FIG. 1, a rectal pressure sensor 31 is inserted into the subject's rectum. The rectal pressure is read and displayed simultaneously with the bladder pressure.

FIGS. 2A and 2B illustrate a preferred embodiment of angle sensor 18. Angle sensor 18 is preferably contained in a housing 38, which is shown partially cutaway in FIGS. 2A and 2B. Angle sensor 18 comprises one or more Hall effect sensors 40, preferably two such sensors in substantially perpendicular mutual orientation, which are disposed in propinquity with a magnet 42. Magnet 42 preferably is fixedly mounted on a float 44 which floats in a liquid 46. Liquid 46 is preferably sealably contained in an inner container 48. Sensors 40 may be mounted on an outer wall of inner container 48.

As seen in FIG. 2B, a spatial angle change in axis 12 of urethra 14, indicated by an arrow 50, causes a corresponding movement of magnet 42 which is sensed by Hall effect sensors 40, thereby sensing spatial angle change 50.

Figures 3A, 3B:
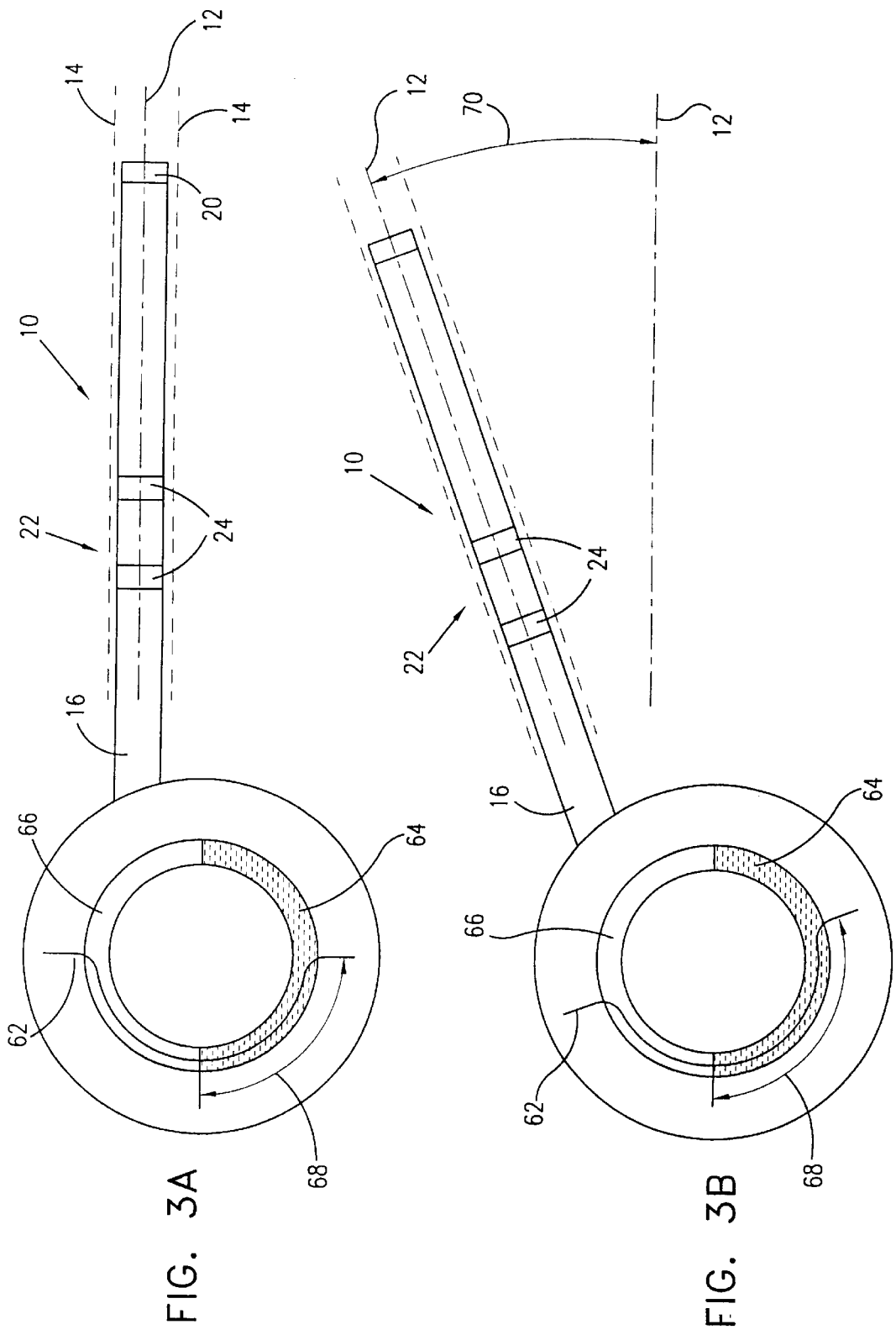
FIGS. 3A and 3B are simplified, partially sectional side view illustrations of the apparatus of FIG. 1 with an angle sensor which comprises a resistive element partially submerged in a conductive fluid, before and after a spatial angle change in the urethral angle, respectively.

FIGS. 3A and 3B illustrate another preferred embodiment of an angle sensor 60. Angle sensor 60 preferably includes a resistive element 62, such as a NICHROME wire, partially submerged in a conductive fluid 64, such as liquid mercury. Conductive fluid 64 is preferably sealed in a generally cylindrical vial 66.

The portion of resistive element 62 which is covered by conductive fluid 64 varies with the angle of probe 16. For example, as seen in FIG. 3A, a portion 68 of resistive element 62 is submerged in conductive fluid 64. In FIG. 3B, a spatial angle change of axis 12, indicated by an arrow 70, causes a corresponding increase in the length of portion 68. The electrical resistance of resistive element 62 varies with the amount of the portion submerged in conductive fluid 64. The measured resistance is transmitted to CPU 26 (not shown in FIGS. 3A and 3B) which converts the resistance into an angular value to determine the change in urethral angle.

FIGS. 4A and 4B illustrate yet another preferred embodiment of apparatus 10, comprising a disposable probe 70, which is inserted into urethra 14, as described above, and a reusable sensor unit 72, to which the probe is coupled, preferably by means of a quick-connect fitting, as is known in the art. Probe 70 is preferably manufactured and supplied to users thereof as a sterile unit, along with a sterile sleeve 74. Sensor unit 72, on the other hand, is not necessarily sterile, and therefore, after probe 70 is coupled to sensor unit 72, sleeve 74 is unrolled over the sensor unit, to prevent contamination of the probe.

Probe 70 includes two lumens 78 and 80, which are preferably concentric, both lumens communicating with respective ports at a distal tip 76 of the probe, which is inserted into the subject's bladder. Lumen 80 communicates with a diaphragm 84 at the proximal end of the probe, which is used in measuring pressure in the bladder, as described below. Lumen 78 communicates with a fluid port 82 near the proximal end of probe 70 and is used to pump fluid into the bladder, so that bladder pressure can be controlled while diagnostic measurements are made as a function thereof. These measurements preferably include measuring leak point pressure using leakage sensor 22, comprising rings 24, as described above.

As shown in FIG. 4B, diaphragm 84 forms a flexible fluid barrier between lumen 80 in disposable probe 70 and sensing circuitry 86 in reusable sensor unit 72. The sensing circuitry detects pressure on or displacement of the diaphragm, in order to measure the pressure in the lumen (and hence in the bladder) without coming into contact with the fluid. After each use, probe 70, including diaphragm 84, is disposed of, while sensor unit 72 is reused. Sensing circuitry preferably further includes a solid-state angle sensor, most preferably a chip accelerometer, as described above, and is electrically connected to rings 24 for measurement of bladder leakage.

Reference is now made to FIG. 5 which is a simplified electronic block diagram of CPU 26 and monitor 30 useful in the apparatus of FIG. 1. In a preferred embodiment of the present invention, signals from angle sensor 18, bladder pressure sensor 20, leak detector 22 and rectal pressure sensor 31 are processed by an analog device 92 and transmitted to a multiplexer 94. CPU 26 samples data from multiplexer 94 preferably via an analog-to-digital converter 96. CPU 26 may alternatively sample data received from sensors 18, 20 and 31 and leakage detector 22, process the data and display pertinent information on monitor 30.

In preferred embodiments of the present invention, a physician inserts probe 16 (or equivalently, probe 70) into urethra 14 of an incontinent subject, and then reads and analyzes angle, pressure and leakage data from display 30 to determine whether the incontinence is the result of urethral hypermobility or intrinsic sphincter deficiency (ISD). Preferably, rectal pressure sensor 31 is inserted into the subject's rectum, and data are received therefrom and analyzed together with the data from probe 16. Alternatively or additionally, the CPU may be programmed to analyze the data and assess automatically the likely cause of the incontinence.

It is appreciated that various features of the invention which are, for clarity, described in the contexts of separate embodiments may also be provided in combination in a single embodiment. Conversely, various features of the invention which are, for brevity, described in the context of a single embodiment may also be provided separately or in any suitable subcombination.

It will be appreciated by persons skilled in the art that the present invention is not limited by what has been particularly shown and described hereinabove. Rather the scope of the present invention is defined only by the claims which follow:

What is claimed is:

1. Apparatus for diagnosing urinary stress incontinence of a subject, comprising:
   a substantially rigid, disposable probe insertable into the urethra of the subject, generally along a longitudinal axis of the urethra; and
   a reusable sensor unit, removably coupled to the probe, for sensing physiological parameters of the subject.

2. Apparatus according to claim 1, and comprising a fluid pressure sensor in pressure communication with a distal end of the probe.

3. Apparatus according to claim 2, wherein the pressure sensor is contained in the sensor unit, and wherein the probe comprises a flexible diaphragm in fluid communication with the distal end, which diaphragm provides the pressure communication between the pressure sensor and the distal end while substantially preventing fluid communication between the distal end and the pressure sensor.

4. Apparatus according to claim 3, wherein the probe contains first and second lumens communicating with the distal end thereof, the first lumen communicating at its proximal end with the diaphragm, and the second lumen communicating at its proximal end with a fluid port.

5. Apparatus according to claim 1, and comprising at least one spatial angle sensor coupled to said probe, so as to sense a change in an angular orientation thereof.

6. Apparatus according to claim 5, wherein the at least one angle sensor comprises a magnet which floats on a liquid, and at least one Hall effect device located in propinquity with the magnet, wherein the change in angular orientation causes a corresponding movement of the magnet, which movement is detected by the at least one Hall effect device, thereby to sense the change.

7. Apparatus according to claim 5, wherein the at least one angle sensor comprises a resistive element partially immersed in a conductive fluid, wherein an amount of the element that is immersed changes in relation to the change in angular orientation, causing a resistive change responsive to the change in angular orientation.

8. Apparatus according to claim 5, wherein the at least one angle sensor comprises a chip accelerometer.

9. Apparatus according to claim 1, and comprising a leakage detector attached to the probe, which detects the flow of a fluid along the probe.

10. Apparatus according to claim 9, wherein the leakage detector comprises an electrical conductivity sensor which detects presence of urine by sensing a change in conductivity due to urine contacting the sensor.

11. Apparatus according to claim 10, wherein the conductivity sensor comprises at least two conductive contacts on an outer surface of the probe.

12. Apparatus according to claim 1, and comprising a flexible sleeve, fixed to the probe, which sleeve is extended over the sensor unit to prevent transfer of contaminants between the probe and the sensor unit.

13. Apparatus according to claim 1, and comprising a central processing unit (CPU) in communication with the sensor unit, for processing data received therefrom.

14. Apparatus according to claim 13, wherein the CPU is in wired communication with the sensor unit.

15. Apparatus according to claim 13, and comprising a wireless transmitter, for transmitting data from the sensor unit to the CPU.

16. Apparatus according to claim 13, and comprising a monitor in electrical communication with the CPU which displays information provided by the CPU.

17. Apparatus according to claim 13, and comprising a rectal pressure sensor in communication with the CPU, which receives and processes data therefrom.

18. A method for diagnosing urinary stress incontinence of a subject, the method comprising:
   coupling a sensor unit to a probe;
   inserting the probe into the urethra of the subject, generally along a longitudinal axis thereof;
   receiving signals from the sensor unit responsive to a change in pressure within the subject's bladder.

19. A method according to claim 18, wherein coupling the sensor unit to the probe comprises bringing a flexible diaphragm, in fluid communication with a distal end of the probe, into pressure communication with the sensor unit.

20. A method according to claim 19, and comprising filling the bladder with fluid through a lumen in the probe, such that the fluid exerts a pressure on the diaphragm, wherein receiving signals from the sensor unit comprises measuring the pressure exerted on the diaphragm.

21. A method according to claim 18, wherein receiving signals from the sensor unit comprises receiving signals responsive to an angular orientation of the probe, and comprising measuring a change in the angular orientation responsive to the change in pressure.

22. A method according to claim 21, and comprising increasing an abdominal pressure of the subject, thereby causing the angular orientation to change.

23. A method according to claim 18, wherein receiving signals from the sensor unit comprises receiving signals responsive to leakage of urine from the bladder of the subject through the urethra.

24. A method according to claim 23, wherein receiving signals from the sensor unit comprises receiving signals responsive to an angular orientation of the probe and measuring a change in the angular orientation responsive to the change in pressure.

25. A method according to claim 24, and comprising analyzing the data to determine whether the urinary stress incontinence is related to urethral hypermobility or to ISD.

26. A method according to claim 24, and comprising inserting a probe into the subject's rectum and receiving signals therefrom responsive to a rectal pressure.

* * * * *